United States Patent [19]
Johnson

[11] Patent Number: 5,652,398
[45] Date of Patent: Jul. 29, 1997

[54] FIXED-VOLUME INJECTOR WITH BACKFLUSH CAPABILITY

[75] Inventor: Paul H. Johnson, Fremont, Calif.

[73] Assignee: Microsensor Technology, Inc., Fremont, Calif.

[21] Appl. No.: 609,223

[22] Filed: Mar. 1, 1996

Related U.S. Application Data

[63] Continuation-in-part of Ser. No. 393,243, Mar. 3, 1995.
[51] Int. Cl.$^6$ .................................................. G01N 30/00
[52] U.S. Cl. ........................ 73/863.71; 73/823.41; 73/23.42
[58] Field of Search ................. 73/23.41, 23.42, 73/863.11, 863.71–863.73, 864.81, 864.83; 95/86–89; 96/105

[56] References Cited

U.S. PATENT DOCUMENTS

| | | | |
|---|---|---|---|
| 2,841,005 | 7/1958 | Coggeshall. | |
| 2,964,938 | 12/1960 | Fuller. | |
| 3,057,376 | 10/1962 | Agutter et al. | 137/594 |
| 3,372,573 | 3/1968 | Sanford et al.. | |
| 3,431,783 | 3/1969 | Radgens. | |
| 3,559,703 | 2/1971 | Maul et al.. | |
| 4,036,062 | 7/1977 | Cruzan. | |
| 4,173,145 | 11/1979 | Durbin. | |
| 4,353,243 | 10/1982 | Martin. | |
| 4,474,889 | 10/1984 | Terry et al. | 436/161 |
| 4,800,761 | 1/1989 | Spencer. | |
| 4,883,505 | 11/1989 | Lucero. | |
| 4,980,130 | 12/1990 | Metzger et al.. | |
| 5,096,471 | 3/1992 | Sacks et al. | 55/67 |
| 5,205,845 | 4/1993 | Sacks et al.. | |
| 5,209,102 | 5/1993 | Wang et al.. | |
| 5,342,786 | 8/1994 | Capuano et al. | 436/103 |
| 5,487,313 | 1/1996 | Johnson | 73/863.71 |

FOREIGN PATENT DOCUMENTS

US94/09319  8/1994  WIPO.

OTHER PUBLICATIONS

Annino, R. et al., *Process Gas Chromatography—Fundamentals and Applications* 183, 185 (1992).

Cooper, C. et al., *The Analysis of Gases by Chromatography* (Pergamon Press) (1983).

Lee, G. et al., "Recent developments in high speed gas chromatography", *American Laboratory* (Feb. 1989).

MTI Analytical Instruments, "New State-of-the-Art Technology/New Micromachined Backflush Valve", Corporate Brochure.

Pearce, B. et al., "Sample Injection Port for High Pressure Chromatography", 44 *Analytical Chemistry* 1107–1109 (1972).

Photovac International, "10Splus Digital Gas Chromatograph", Part No. 380200 Rev. B; Index and Chapters 10 and 11 (1991).

Terry, S. et al., "A Gas Chromatographic Air Analyzer Fabricated on a Silicon Wafer", ED–26 *IEEE Transactions on Electron Devices* (1979).

Valco Product Literature, date unknown.

*Primary Examiner*—Robert Raevis
*Attorney, Agent, or Firm*—Skjerven, Morrill, MacPherson, Franklin & Friel; Emily M. Haliday

[57] ABSTRACT

A fixed-volume injector assembly having backflush capability is useful for injecting a sample into a gas chromatograph. The injector assembly has a sampling mode of operation, an injection mode of operation and a backflush mode of operation. In the sampling mode, sample is drawn into sampling chamber (11). In the injection mode, sample is injected into an injection channel which conducts the sample to a destination stream. In the backflush mode, carrier fluid flows through the injector assembly in the opposite direction. The injector assembly is designed to connect to precolumn (28) and analytical column (20) so that, in the backflush mode, precolumn (28) is backflushed. Advantages of the injector assembly include the ability to pressurize the sample before injection and to use a single carrier fluid source. In addition, the flow channels of the injector assembly are readily miniaturized.

40 Claims, 10 Drawing Sheets

FIXED-VOLUME INJECTOR WITH BACKFLUSH CAPABILITY

REFERENCE TO RELATED APPLICATION

This application is a continuation-in-part application of prior copending application Ser. No. 08/398,243, filed Mar. 3, 1995, which is hereby expressly incorporated in its entirety herein by reference.

BACKGROUND OF THE INVENTION

1. Field of the Invention

This invention relates to an injector useful in gas chromatography, and more particularly to a micromachined microvalve injector assembly that can inject a fixed volume of a fluid sample into a destination stream. The injector assembly also includes valving to reverse fluid flow through the injector, which facilitates sample analysis by the column backflush technique.

2. Description of the Prior Art

Gas chromatographs are well known for analysis of chemical mixtures, separation of gases, and process measurement and control. A gas chromatograph includes three main components: an analytical column which physically separates the components of a sample mixture, a detector which senses the individual components after separation, and an injector which introduces an amount of the sample into the analytical column for separation.

The detector is located at the outlet of the analytical column. The detector generates a printout showing peaks corresponding to the sample components (termed a "chromatogram"). These results are typically analyzed by comparing the sample profile with the profile obtained for a calibration fluid of known composition.

The injector introduces a "plug" of sample into the analytical column. As injection time increases, the peaks detected by the detector tend to broaden and overlap. Therefore, the plug is ideally injected over the shortest possible period time. For quantitative analysis, the injector must introduce a controlled amount of sample into the precolumn or analytical column. The most common injection techniques for gas chromatography are by syringe and by sample loop.

The well-known sample loop injector includes a two-position multiport rotary valve. The sample loop is filled with sample while a carrier gas flows to the analytical column through channels in the valve. When the valve rotor is turned to move the valve into the second position, the arrangement of valve channels is re-configured, and the sample loop becomes part of the channeling that conducts the carrier gas through the valve to the analytical column. In the second position, the carrier gas flow sweeps the sample from the sample loop. Sample thus flows in the carrier gas stream to the analytical column.

A variation on the sample loop is used in the 10S series gas chromatograph manufactured by Photovac International. Four solenoid valves are used to isolate the sample loop during filling with sample and insert the sample loop into the carrier gas stream during the sample injection event.

U.S. Pat. No. 4,474,889, entitled "Miniature Gas Chromatograph Apparatus" (issued on Oct. 2, 1984, and incorporated by reference herein), commonly owned with the present application, describes a sample injection scheme that utilizes a miniaturized injector. In addition to being smaller and more convenient to use, miniaturized injectors have reduced injection times. Accordingly, such injectors provide better resolution and facilitate high-speed chromatographic analysis.

The injector disclosed in U.S. Pat. No. 4,474,889 employs a "timed-injection" scheme, wherein the amount of injected sample depends on the period of time that an inject valve is open. However, the amount of sample that flows into the analytical column during a particular injection time decreases undesirably as the sample viscosity increases. Therefore, the reported response (peak area) of the associated gas chromatograph for a particular analyte decreases as the sample viscosity increases.

A recent disclosure, the "Fluid-Lock Fixed Volume Injector" (U.S. patent. application Ser. No. 08/158,978, filed on Nov. 30, 1993), commonly owned with the present application, is directed to a miniature injector that injects a fixed-volume of sample fluid without regard to fluid viscosity.

Neither of these disclosures is directed to a "backflush" capability. With respect to gas chromatography, "backflush" typically refers to the reversal of carrier gas flow through a "precolumn" that is connected in series to an analytical column. The "precolumn" is located between the sample injector and the analytical column. The injected sample flows first into the precolumn, then into the analytical column. In practice, after some of the sample components reach the analytical column, the flow through the precolumn is reversed or stopped. The sample components thereby isolated on the precolumn are processed separately from those sample components that had entered the analytical column.

The sample components in the precolumn are typically swept from the precolumn to a vent or to a detector, using carrier gas flowing in the direction opposite to the original sample flow direction. Analytical column backflushing is also possible. In this case, the gas chromatograph may contain only an analytical column.

Some conventional gas chromatograph injectors having backflush capability use a combination of rotary valves to achieve sample and carrier gas flow switching. Such rotary valves have the disadvantage of being difficult to miniaturize. In addition, relatively large dead volumes and slow switching times limit the performance of rotary sample valves. Furthermore, rotary valves undergo a limited number of cycles before the valves wear out due to friction at the seal interface.

The Photovac 10S series gas chromatograph uses solenoid valves to achieve precolumn backflush. Like rotary valves, solenoid valves are difficult to miniaturize. Moreover, solenoid valves can be susceptible to air diffusion and contamination by sample components. Both the entry of air into injector flow channels and valve contamination undermine gas chromatograph performance.

There is a need for a fixed-volume backflush sample injector that avoids the drawbacks of conventional injectors. In particular, a fixed-volume injector that can be miniaturized easily, is unaffected by variations in sample viscosity, and can provide the sample and carrier gas flow switching required for backflush operation would be desirable.

SUMMARY OF THE INVENTION

The present invention is directed to a fixed-volume injector assembly having backflush capability. The injector assembly injects the same volume of sample fluid, despite variations in sample fluid viscosity. In one embodiment, the injector assembly is a micromachined, microvalve assembly. The injector assembly is described herein as an injector for a gas chromatograph by way of illustration and not byway limitation.

The injector assembly of the present invention has a sampling mode of operation, an injection mode of operation and a backflush mode of operation. In the sampling mode, sample is drawn into a sampling chamber. In the injection mode, sample is injected into an injection channel which conducts the sample to a destination stream. In the backflush mode, carrier fluid flows through the injector assembly in the opposite direction.

A portion of the sample chamber is designed to contain the fixed volume of the sample to be injected. This portion of the chamber is therefore termed the "fixed-volume" portion. A sample valve is connected to the sample chamber at one end, for filling the sample chamber. The sample chamber is open at the other end. The open end is adapted to connect to a means for trapping sample in the sample chamber.

A purge/foreflush valve is connected to one end of the fixed-volume portion of the sample chamber. In the injection mode, a purge fluid enters the sample chamber, thereby forcing sample into an injection channel that conducts the sample to a destination stream. When the injector is employed with a gas chromatograph, the destination stream enters a column.

An inject valve is connected to the end of the fixed-volume portion of the sample chamber opposite the purge/foreflush valve. In the injection mode, the inject valve conducts sample from the fixed-volume portion of the sample chamber to the injection channel. In the backflush mode of operation, carrier fluid flows from a carrier fluid source connected to the injection channel and through the inject valve in the opposite direction.

A backflush valve is located between the inject valve and the carrier fluid source. In the backflush mode, the backflush valve conducts carrier fluid toward the inject valve.

In one embodiment, a pressurization valve is connected to the open end of the sample chamber. This valve opens prior to injection, allowing a pressurization fluid to enter the sample chamber, which traps and pressurizes the sample.

Thus, in the sampling mode, the foreflush and inject valves are closed, and the sample and backflush valves are open. Sample gas flows through the sample valve, through the sample chamber, past the inject valve and the purge/foreflush valve to a vent. After sampling, the sample valve is closed, and pressure is applied by switching the pressurization valve to trap and pressurize the sample.

During sample injection (also termed "foreflush") the backflush valve is closed, the inject valve and purge/foreflush valves are opened, and the pressurization valve is switched to connect the sample chamber to the vent. Purge fluid flows through the purge/foreflush valve into the sample chamber and forces sample in the fixed-volume portion of the sample chamber through the inject valve into the injection channel. Thus, the purge fluid entering the sample chamber forms a "fluid-lock" that segregates the sample in the sample chamber into two parts: the fixed-volume part which flows through the inject Valve and the remainder which exits through the sample vent.

The injection channel can be connected to one end of an analytical column at a point between the inject valve and the backflush valve. In addition, a precolumn can be incorporated into the injection channel between the analytical column and the inject valve. In this embodiment, the injection channel comprises first and second segments separated by a space for the precolumn. The first segment is connected at one end to the inject valve, and the second segment is connected at one end to the analytical column.

The unconnected ends of the injection channel segments are adapted to connect to the ends of a precolumn, so that fluid flowing from the inject valve flows through the first segment, the precolumn, and the second segment and then enters the analytical column. In this configuration, the injector assembly backflushes the precolumn while maintaining normal forward flow over the analytical column.

Backflush is initiated at a time after injection when selected components have exited the precolumn. To initiate backflush, the purge/foreflush valve is closed, and the backflush valve is opened. Carrier fluid flows through the backflush valve to the analytical column, and the sample components in the analytical column further segregate while the sample flows through the analytical column to the detector. Carrier fluid also flows through the backflush valve, the precolumn, the inject valve, the sample chamber, and out the vent, thereby removing the sample components from the precolumn. In a variation of this embodiment, a detector is inserted between the precolumn and the inject valve. This variation allows the detection of sample components as they are flushed off of the precolumn during backflushing.

The injector assembly of the present invention has the advantage that the purge fluid, the pressurization fluid, and the carrier fluid can be derived from a common fluid source.

For high accuracy analyses, it is desirable to control the sample temperature because variations in sample temperature affect the amount of sample trapped in the fixed-volume portion of the sample chamber. Therefore, in one embodiment, the sample temperature is thermostatically-controlled.

In one embodiment, the injector assembly comprises a multilayered microvalve injector assembly that includes a layer micromachined from a silicon wafer. The valves in this embodiment are diaphragm valves. In a variation of this embodiment, a heater is integrated into one of the layers of the microvalve assembly. In accordance with this embodiment, a resistive trace heater and associated resistive trace sensor can deposited on the surface of one of the layers for thermostatically-controlled heating of the microvalve assembly and the sample chamber.

The invention can operate as a simple fixed-volume injector if the precolumn is replaced by an inert channel that conducts sample and carrier fluid flows between the inject valve and the backflush valve. In this embodiment, the invention can also operate as a timed injector, by pressurizing the sample, then opening the inject valve with the foreflush and backflush valves closed.

The injector assembly of the present invention is significantly different from existing injectors. In particular, the present injector assembly uses pressurized fluid to trap and pressurize sample in a chamber, thereby achieving a more reproducible injected sample volume. Conventional injectors, such as that in the Photovac 10S series, use valves to trap the sample. Furthermore, the injector assembly of the present injection employs a purge fluid stream to isolate the fixed-volume portion before injection. These features of the present injector assembly facilitate miniaturization and render the injector assembly less susceptible to the problems associated with rotary and solenoid valves.

In addition, the injection assembly has three valves that communicate directly with the sample chamber, which has an open end for connecting the sample chamber to means for pressurizing the sample. In the Photovac injector, by contrast, the sample chamber is closed, and only two valves communicate directly with the sample chamber.

The injector assembly of the present invention also differs from the previously described "Fluid-Lock Fixed Volume Injector" (U.S. patent application Ser. No. 08/158,978, filed on Nov. 30, 1993) in that the present injector assembly comprises an additional valve, the backflush valve. In addition to facilitating precolumn backflushing, this backflush valve allows the present injector assembly to operate on a single carrier. fluid source at a selected pressure, whereas the Fluid-Lock injector requires carrier fluid at two different pressures.

The above and other objects, features and advantages will be clear from the following detailed description of the invention in conjunction with the accompanying drawings.

DETAILED DESCRIPTION OF THE INVENTION

Figure 1:
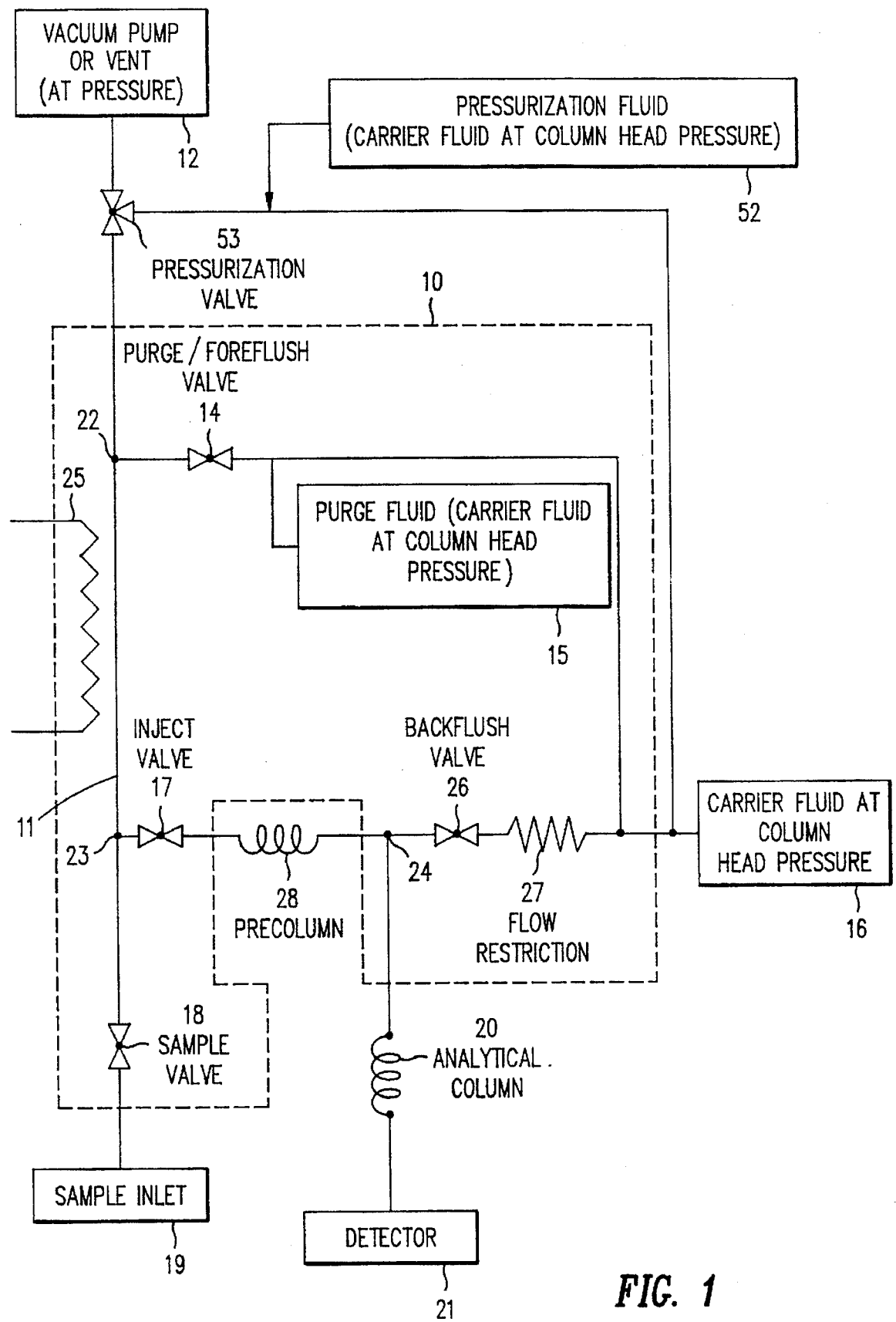
FIG. 1 is a schematic diagram of a gas chromatograph system including an injector assembly in accordance with an embodiment of the present invention wherein the injection channel comprises a precolumn and a single fluid source supplies the purge fluid, the pressurization fluid, and the carrier fluid.

FIG. 1 is a schematic view of a gas chromatograph system with an injector assembly in accordance with one embodiment of the present invention. The gas chromatograph system includes precolumn 28 and analytical column 20. Precolumn 28 and analytical column 20 are made from conventional capillary columns or similar narrow-bore packed columns. In a variation of this embodiment, a detector (not shown) can be inserted between the precolumn and the inject valve. This variation allows the detection of sample components as they are flushed off of the precolumn during backflushing.

In addition, the gas chromatograph system includes carrier fluid source 16 which supplies purge fluid 15 (carrier fluid at column head pressure) and pressurization fluid 52 (carrier fluid at column head pressure), in addition to carrier fluid. The purge, pressurization, and carrier fluids can be any appropriate fluid for the particular embodiment that is inert relative to the fluid sample and the column materials. Other considerations are cost, availability, and ease of use in a particular embodiment.

Injector assembly 10 is contained within the dotted line. Sample chamber 11 is sealed at one end by sample valve 18 and at the other end by the application of pressurized fluid from pressurization valve 53. Pressurization valve 53 is a switch valve that toggles between connecting the sample chamber to pressurization fluid 52 and vacuum pump or vent 12. Sample chamber 11 is essentially the space available for filling with sample between sample valve 18 and pressurization valve 53.

Sample enters the gas chromatograph system at the sample inlet 19. The sample may be pressurized, and hence flow under its own pressure, or may be drawn in and through the sample chamber 11 using a vacuum pump at 12. After filling sample chamber 11 with sample, sample valve 18 is closed.

A period of time, termed the "dwell time", is then required to allow sample temperature and pressure to equilibrate for effective operation of the injector assembly. For example, if sample is introduced into the sample chamber under its own pressure, then dwell time is needed for excess sample to vent out of the sample chamber through vacuum pump or vent 12. The dwell time duration depends on particular dimensions of the sample chamber, the pressures used, and other details specific to the particular embodiment of the invention.

At the end of the dwell time, pressurization valve 53 is actuated to connect sample chamber 11 to pressurization fluid 52. Pressurization fluid 52 traps the sample in sample chamber 11 and pressurizes the sample to the pressure of pressurization fluid 52 over a period of time termed the "pressurization time". The pressurization time is the length of time necessary for the sample in the sample chamber to attain a reproducible temperature and pressure before the sample injection event. The pressurization time depends on the particular chamber and channel structure and the pressure of the pressurization fluid.

There are optimal dwell and pressurization times or ranges of times for each particular configuration of an apparatus in accordance with the invention, which can be determined experimentally. Particular sequences and timing of the actuations of purge/foreflush valve 14, inject valve 17, sample valve 18, backflush valve 26, and pressurization valve 53 are determined similarly to optimize results. The sequence and timing of valve actuations that gives the most reproducible sample injection volume over the range of operation variables relevant to the particular embodiment (for example, variation in sample inlet pressure) is selected for use. Determination of optimal dwell and pressurization times as well as the sequence and timing of valve actuations is a matter of mere routine and therefore within the level of skill in the art.

To initiate sample injection, purge/foreflush valve 14 and inject valve 17 open, backflush valve 26 closes, and pressurization valve 53 connects to vacuum pump or vent 12. Purge fluid (which is carrier fluid in this embodiment) flows from purge/foreflush valve 14 into sample chamber 11 at junction 22. The portion of sample chamber 11 between the orifice of purge/foreflush valve 14 and the orifice of inject valve 17 is the "fixed-volume" portion of the sample chamber. The flow of purge fluid forces sample in the fixed-volume portion of sample chamber 11 to flow through the inject valve 17 into the injection passage, which comprises precolumn 28. Thus, the flow of purge fluid effects the injection of a fixed volume of sample.

With backflush valve 26 closed, the purge fluid emitted by the purge/foreflush valve 14 serves as the carrier fluid that carries sample components over the columns. As the injected sample flows through precolumn 28, the sample components separate. When selected sample components exit precolumn 28 and pass junction 24, backflush valve 26 is opened and purge/ foreflush valve 14 is closed.

The sample components that passed junction 24 before backflush valve opening flow onto analytical column 20 for analysis, where sample components separate and are sensed by detector 21 as they exit analytical column 20. The sample components remaining on precolumn 28 are swept from the precolumn by carrier fluid flowing from backflush valve 26 through the precolumn 28 in the direction opposite to the direction of injection flow.

Typically, the time for switching to backflush is determined experimentally. Various times are tried and the resultant chromatograms are studied to determine the time that gives the desired separation of sample components. However, incorporating an additional nondestructive detector between the precolumn and analytical column is also possible. The output of such a detector would be used to determine when the sample components have exited the precolumn and hence the appropriate time for switching to backflush.

In this embodiment, conventional carrier fluid source 16 is connected to injector assembly 10 to provide a regulated carrier fluid pressure at "column head pressure". A channel in injector assembly 10 conducts the carrier fluid from source 16 to purge/foreflush valve 14, thereby providing purge fluid 15. Carrier fluid source 16 is also connected to pressurization valve 53, thereby providing pressurization fluid 52.

In addition, carrier fluid source 16 provides carrier fluid which flows through flow restriction 27 to backflush valve 26. Flow restriction 27 lowers the pressure in precolumn 28 to below column head pressure, so that the purge fluid pressure is sufficient to force the sample in the fixed-volume portion sample chamber 11 into precolumn 28 during injection. Flow restriction 27 is optional. However, if flow restriction 27 is omitted, the pressure in precolumn 28 must be reduced prior to injection, for example, by closing backflush valve 26 before opening inject valve 17 and allowing the some carrier fluid downstream of inject valve 17 to vent through detector 21. If the pressure in precolumn 28 is higher than the sample chamber or purge fluid pressures, the excess pressure in the precolumn 28 can induce flow into sample chamber 11, thereby displacing the sample undesirably.

For some embodiments, a "purge" sequence is required to clear the fluid pathways of undesirable fluids or trapped materials between analytical runs, prior to putting the injector assembly into service, or as part of a "warm-up" procedure. This purge/clear sequence involves opening the appropriate valves in the appropriate sequence to purge one or more selected fluid paths within the injector. For example, it may be desirable to open the purge/foreflush valve during warm-up for a time sufficient to allow carrier fluid to flow through the injector assembly to vent trapped air.

Alternatively, the backflush and inject valves can be opened to clear sample residues from the inject valve and sample Chamber to reduce sample carryover and calibration fluid contamination. One skilled in the art can readily determine the appropriate purge/clear sequence for clearing a particular fluid path from the teachings herein.

Sample is not drawn through 14, 17, 22, or 23 during sampling. Because these "unswept" or "dead" internal volumes are part of the fixed-volume portion of the sample chamber, these internal volumes should be as small as possible. Therefore, the performance of injector assembly 10 is improved by minimizing the internal volumes between 14 and 22, between 17 and 23, and between 24 and 26. Minimizing the internal volume between 22 and 53 and between 18 and 23 is also useful to facilitate injector assembly miniaturization, to allow higher speeds of operation, and to minimize the amount of sample required per injection.

Valves 14, 17, and 26 are preferably T-valves to minimize the internal volume between 14 and 22, between 17 and 23, and between 24 and 26. If purge/foreflush valve 14, for example, is a T-valve, the through channel of purge/foreflush valve 14 is connected to and forms a part of sample chamber 11. The branched channel of purge/foreflush valve 14 is connected to purge fluid 15. When purge/foreflush valve 14 is opened, purge fluid 15 flows from the branched channel of purge/foreflush valve 14 into the through channel of purge/foreflush valve 14 and spreads in both directions (towards 23 and 53) in sample chamber 11.

The above-described embodiment allows for precolumn backflushing. However, analytical column backflushing is also possible. In this embodiment, precolumn 28 in FIG. 1 is replaced with an analytical column and analytical column 20 can be replaced with an inert channel between junction 24 and detector 21. In a variation of this embodiment, a detector can be inserted between the analytical column and the inject valve to detect sample components as they are flushed off of the analytical column during backflushing.

Figure 2:
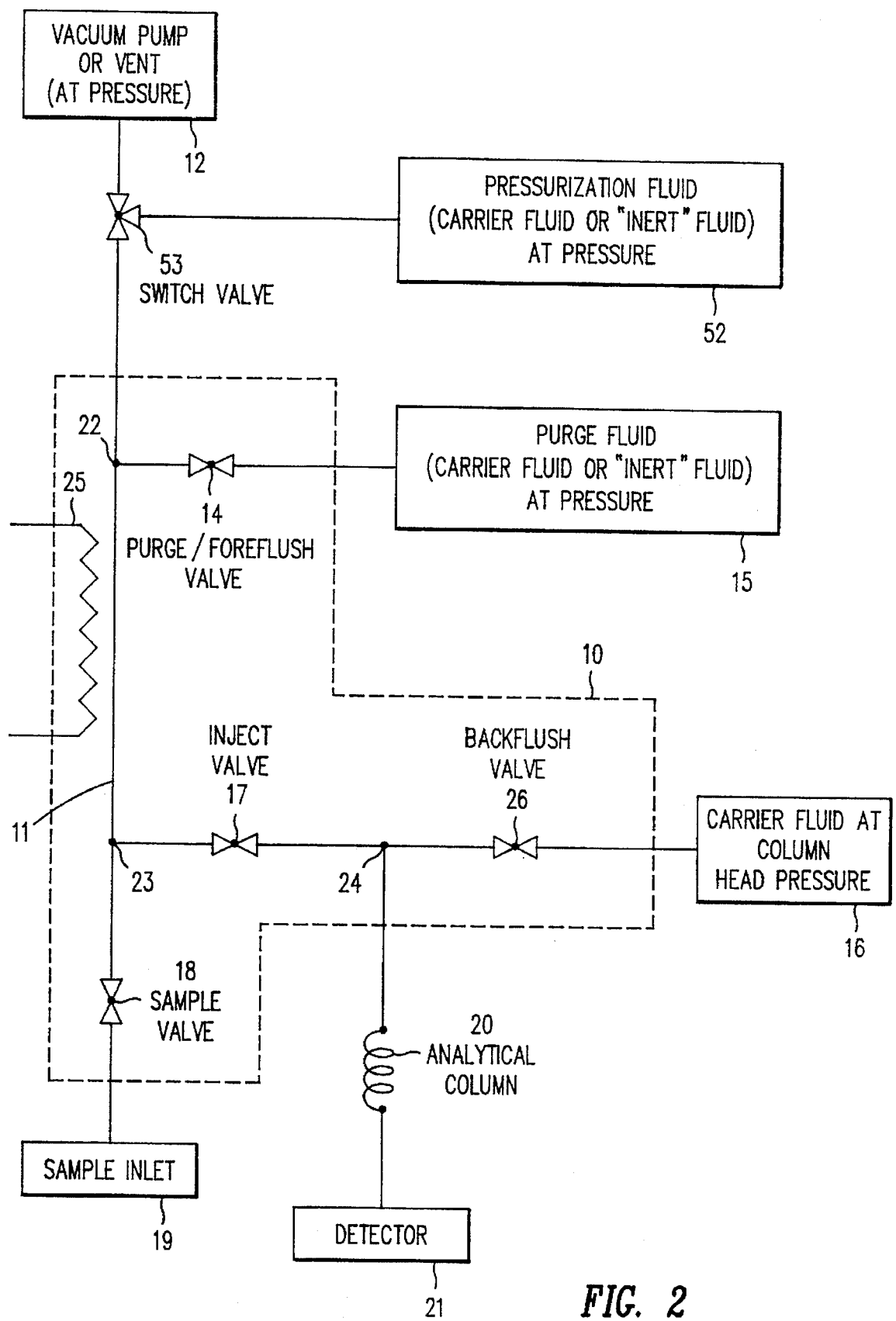
FIG. 2 is a schematic diagram of a gas chromatograph system including an injector assembly in accordance with another embodiment of the present invention wherein an inert channel replaces the precolumn and three gas sources are employed.

FIG. 2 is a schematic view of a gas chromatograph system with an injector assembly in accordance with another embodiment of the present invention. Injector assembly 10 is contained within the dotted line The embodiment of FIG. 2 differs from that of FIG. 1 in two ways. First, FIG. 2 shows that separate sources can be used for purge fluid 15, pressurization fluid 52, and carrier fluid 16.

In practice, the pressures of each source can be approximately the same. However, a purge fluid pressure higher than the carrier fluid pressure and the pressurization fluid pressure is generally optimal. The pressures used influence valve actuation sequence and timing. One skilled in the art can readily determine the appropriate pressures for optimal performance experimentally.

Separate sources 15, 16, and 52 allow for "pressure programming" of purge fluid 15, pressurization fluid 52, and carrier fluid 16. That is, the pressures of these fluids can be increased or decreased in a selected sequence. Alternatively, the compositions of purge fluid 15, pressurization fluid 52, and carrier fluid 16 can be programmed to vary in a controlled manner, independent of one another. Suitable pressure or fluid composition programs can be designed to enhance the performance of the injector assembly and any system incorporating it.

The second difference between the embodiments shown in FIGS. 1 and 2 is that precolumn 28 of FIG. 1 is replaced in FIG. 2 with an inert channel between inject valve 17 and junction 24. This embodiment operates as a fixed-volume injector assembly without the precolumn backflush feature. The operation of the FIG. 2 embodiment is like that of the FIG. 1 embodiment, except that the injection event is typically shorter, and the inject valve is typically closed after the injection event for the duration of sample analysis.

Figure 3:
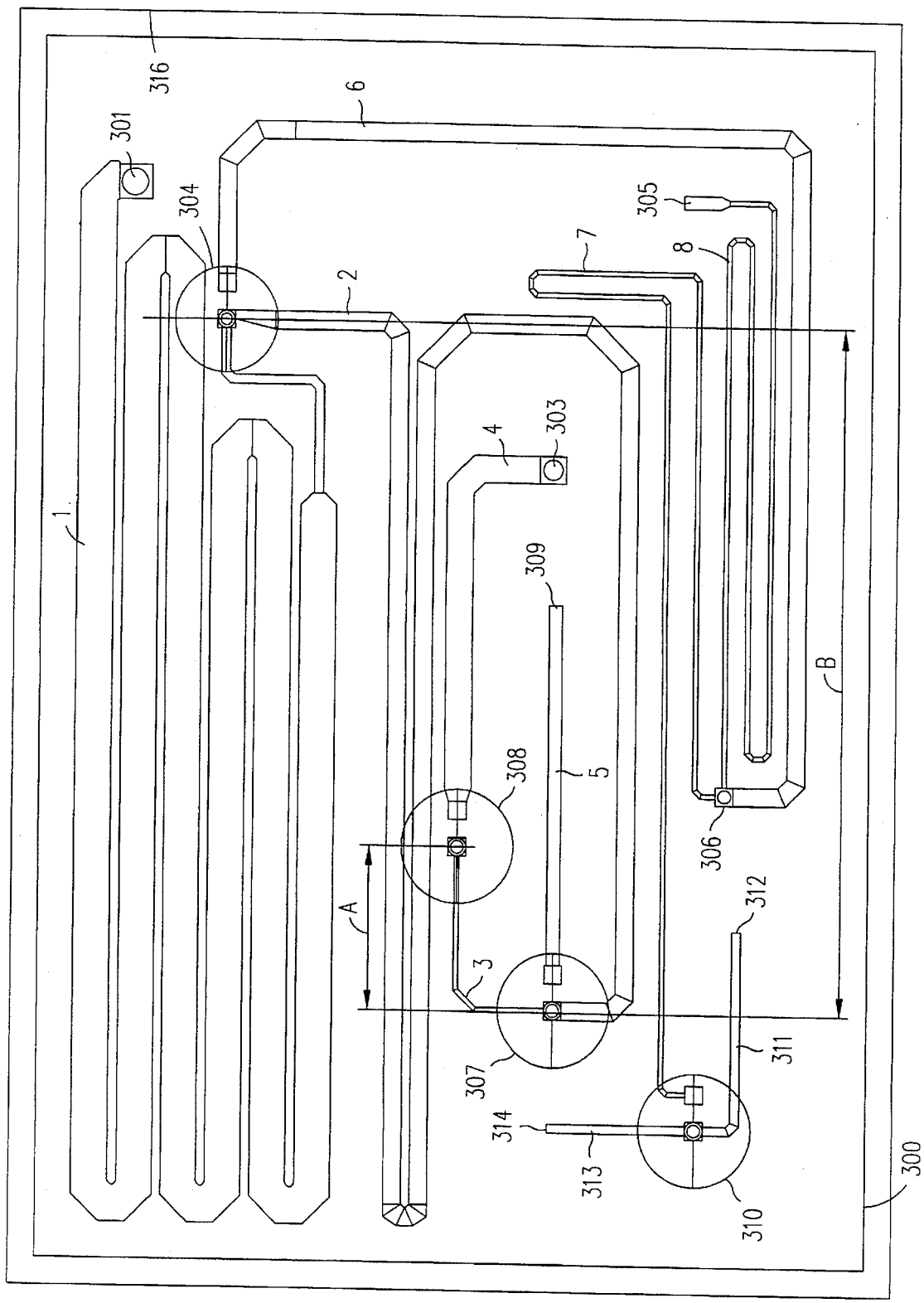
FIG. 3 shows a micromachined microvalve injector assembly of the present invention corresponding to FIG. 1.
Figure 4:
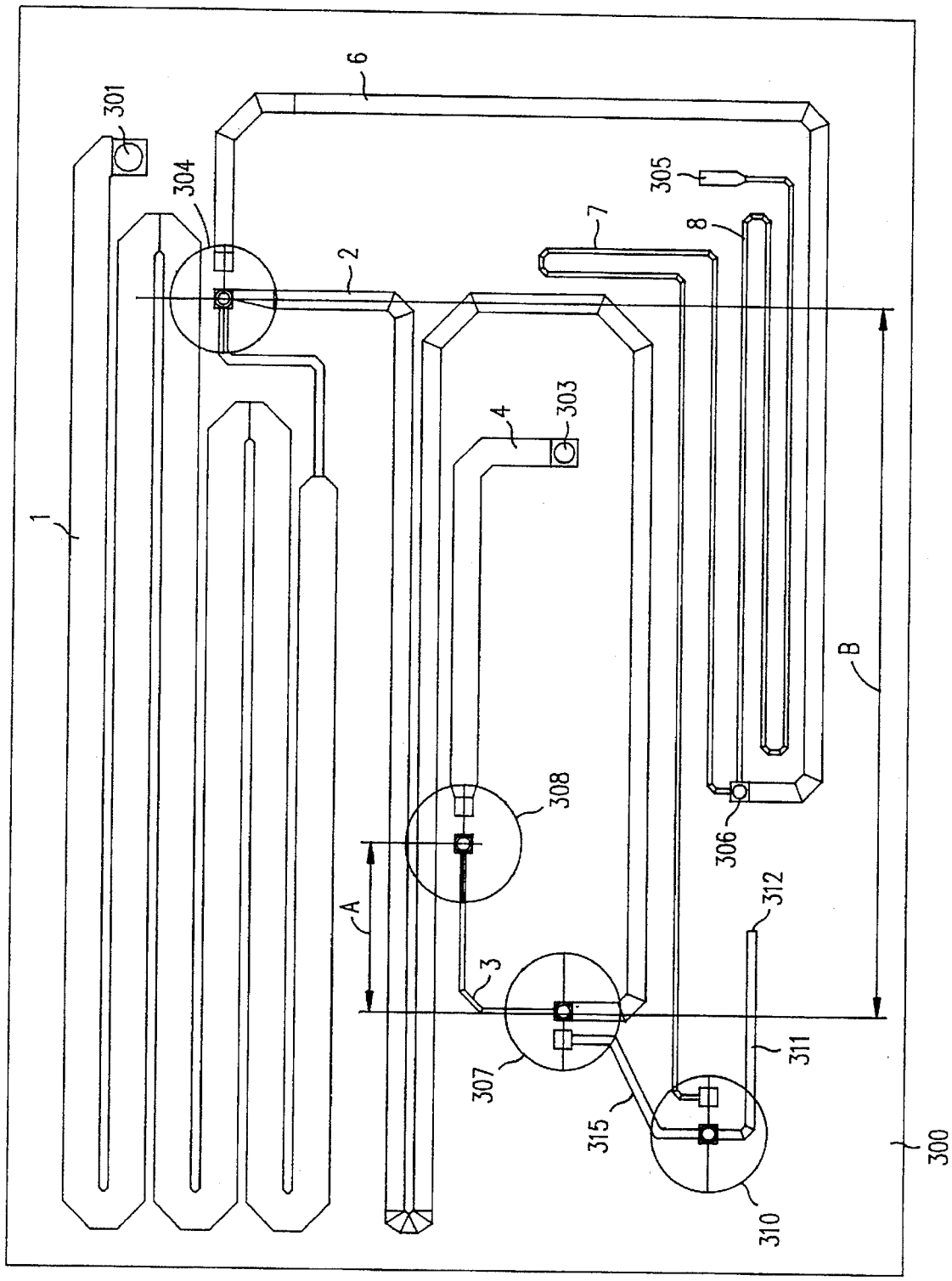
FIG. 4 shows a micromachined microvalve injector assembly of the present invention corresponding to FIG. 2.

FIGS. 3 and 4 show two different micromachined microvalve injector assembly embodiments. In such embodiments, the valves are preferably micromachined diaphragm valves. When the diaphragm of the valve is subject to pressure, the diaphragm valve closes. When the pressure applied to the diaphragm is released, the valve opens. The control pressure applied to the diaphragm of the valves should be significantly higher than that of the fluid stream being controlled, so that the diaphragm seals adequately against the pressure of the fluid stream being controlled.

In FIGS. 3 and 4, wafer 300 used for an injector in accordance with the present invention is micromachined from a silicon wafer using processes that do not differ from conventional silicon micromachining and packaging technology. Briefly, wafer 300 is produced by a series of oxidation, photolithography, and etching steps similar to well-known integrated circuit device processing steps. Through the use of isotropic and anisotropic silicon etches, very small-volume holes, shallow wells, and grooves which form miniature valve seats and capillary channels are precisely fabricated on a silicon wafer.

Figure 5A:
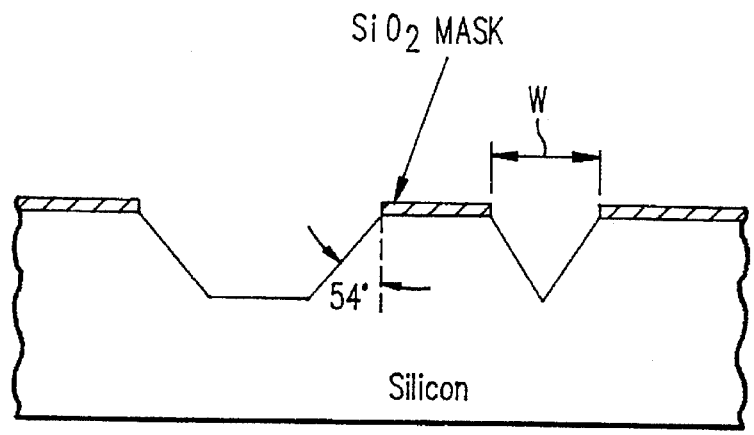
FIGS. 5A–5C show cross sections of grooves etched with KOH etchant in (100) silicon, KOH in (110) silicon, and HF-HNO$_3$ etchant in silicon, respectively.
Figure 5B:
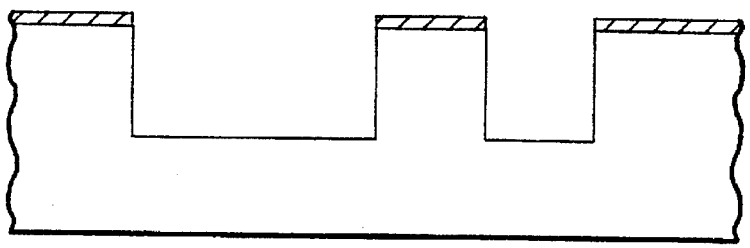

Several groove cross-sectional profiles are available, depending upon the crystallographic orientation of the silicon, the etchant used, etc. An anisotropic etchant such as potassium hydroxide (KOH) results in a V-groove profile in (100) oriented silicon as shown in FIG. 5A. The sides of the "V" are determined conventionally by crystallographic planes in the silicon. For a narrow groove in which the V walls meet, the depth of the groove can be precisely controlled by the width (W) of the opening in the oxide etch mask. In (110) oriented silicon, or along certain crystallographic directions in (100) silicon, KOH etches grooves with a vertical wall as shown in FIG. 5B.

Figure 5C:
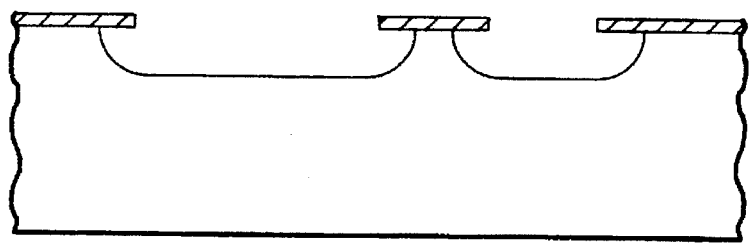

A disadvantage of the anisotropic etches, however, is that the desired groove profiles are achieved only if the grooves lie along specific crystallographic axes, and certain shapes, such as square corners, can be realized; whereas others, such as circles, cannot be realized. A mixture of hydrofluoric and nitric acids (HF—HNO3) can be used as an isotropic silicon etchant to produce the grooves shown in FIG. 5C. This etchant produces approximately rectangular grooves (with rounded corners), oriented in any direction on the wafer, as well as circular valve seats.

Figure 6A:
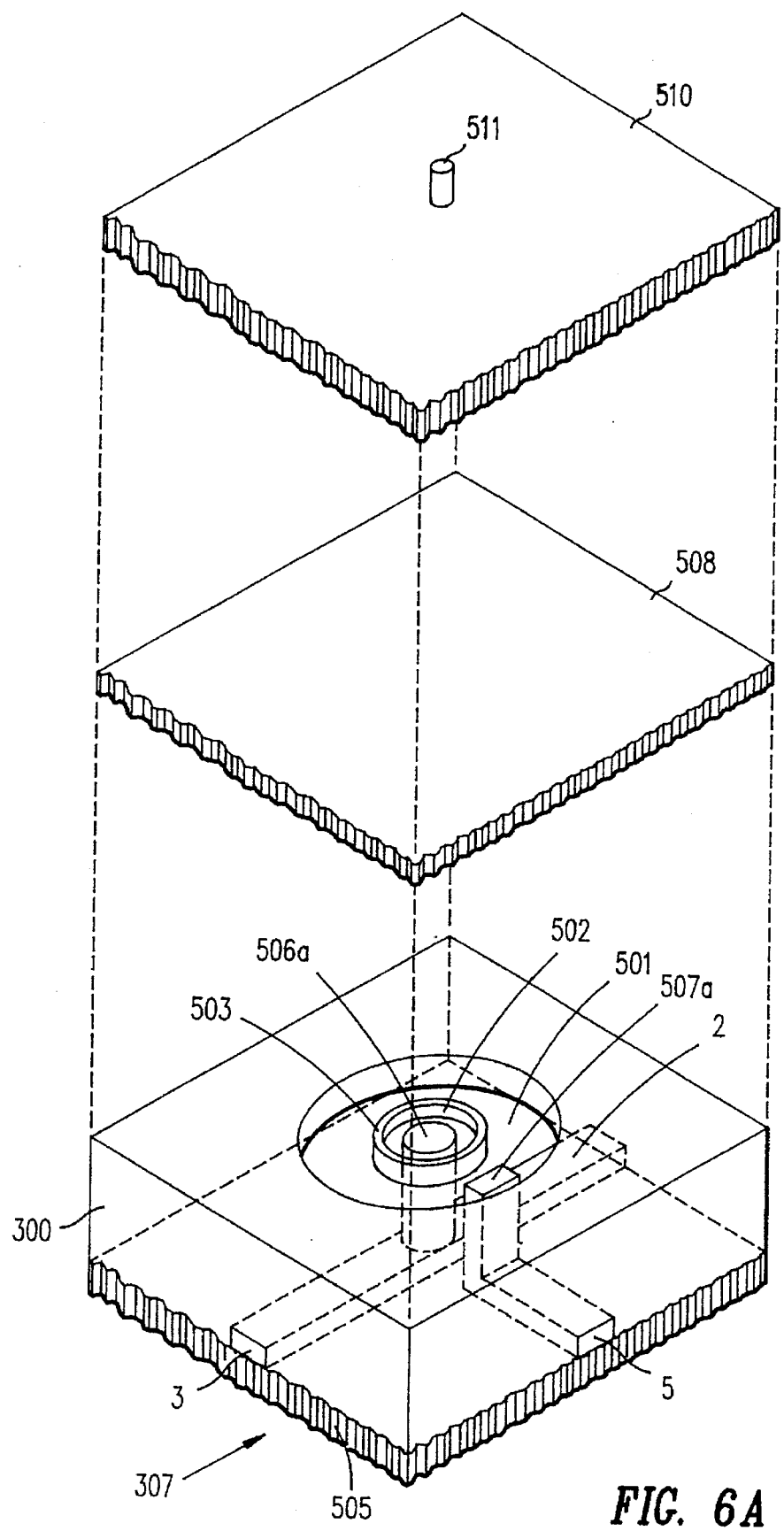
FIGS. 6A–6B are perspective views showing the structures of the microvalves in FIGS. 3 and 4.
Figure 6B:
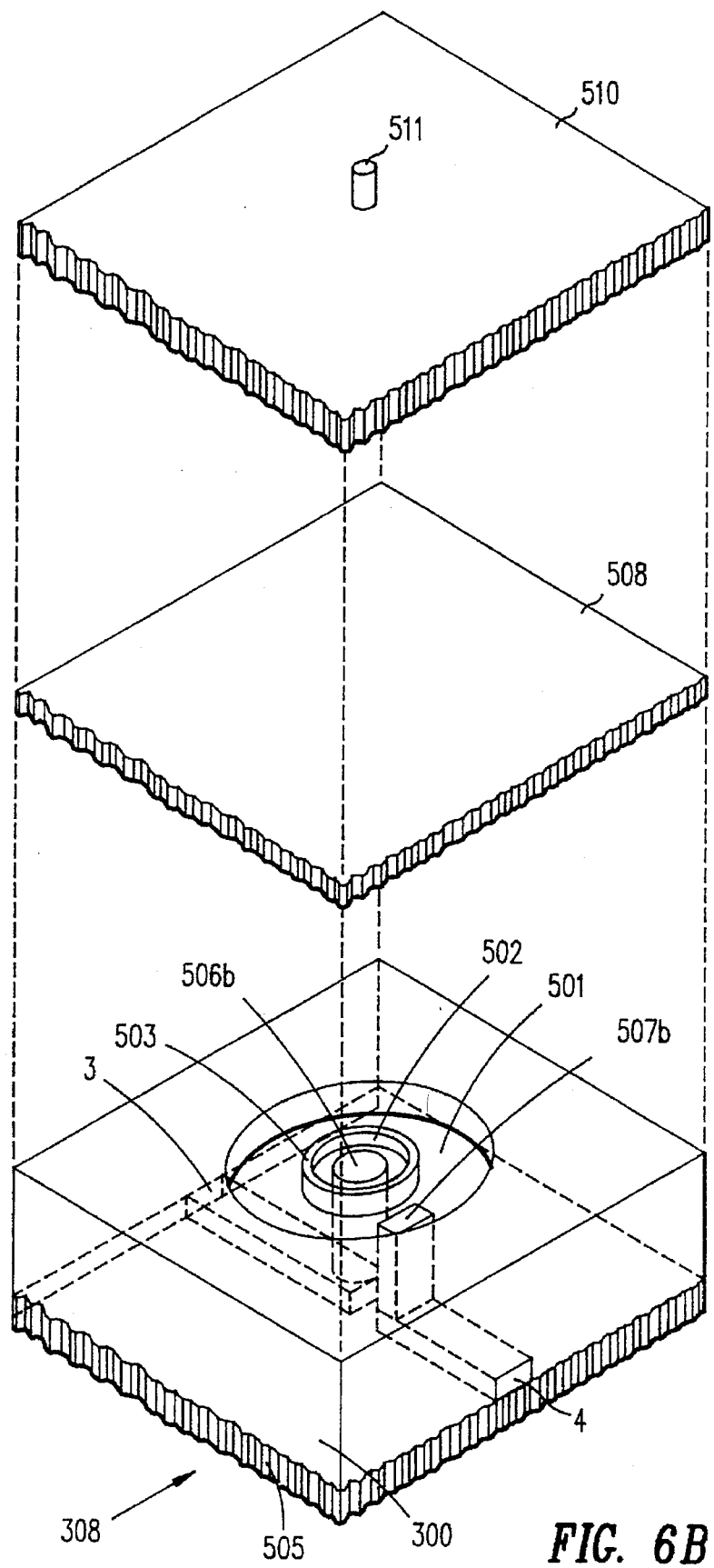

After wafer 300 has been micromachined, wafer 300 is sandwiched between several other layers, which are shown in FIGS. 6A and 6B. An inflexible layer is bonded on to wafer 300 to seal the etched grooves in wafer 300 and thereby form microchannels. (The inflexible layer is therefore said to be on "the microchannel side" of the wafer.) A flexible layer that acts as the diaphragm of valves 304, 307, 308, and 310 (shown in FIGS. 3 and 4) is bonded to the other side of wafer 300 (the "valve seat side"). Another inflexible layer is bonded to the flexible material layer. The "sandwich" thus formed consists of four layers: inflexible layer 505, silicon wafer 300, flexible layer 508, and inflexible layer 510. Although wafer 300 is shown with microchannels and valve seats on opposite sides, it is also possible to form the microchannels and valve seats on the same side of wafer 300.

In one embodiment, Pyrex glass plates are used for the inflexible layers, and the flexible layer is a Dupont product called Kapton (a sheet material consisting of three layers: Teflon, polyimide, Teflon). The Pyrex plate on the microchannel side of wafer 300 is bonded to wafer 300 using a process called "anodic bonding". The Kapton and the other Pyrex plate can be attached by pressing and heating the assembled layers. The Kapton becomes "sticky" when heated, thereby bonding to wafer 300 and the Pyrex plate.

Figure 7A:
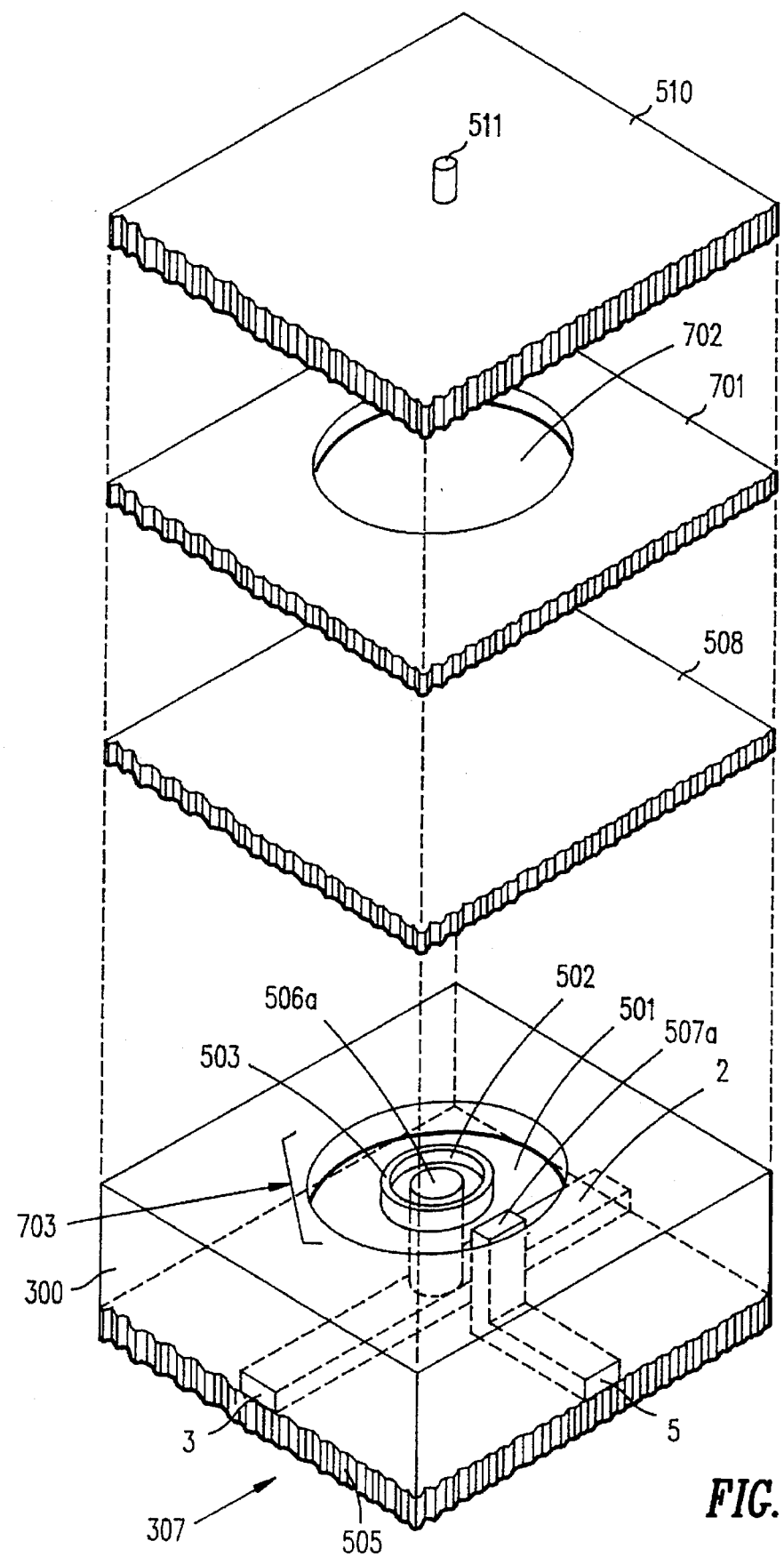
FIGS. 7A–7C show different embodiments of the injector assembly that include structure or a substance for preventing the valve diaphragms of the injector assembly from sticking to an adjacent Pyrex plate upon heating during production.

If this pressing and heating production method is used, the injector assembly includes structure or a substance for preventing the areas of the Kapton layer that form the valve diaphragms from sticking to the adjacent Pyrex plate upon heating. These areas of the Kapton layer must move freely to function as valve diaphragms. FIG. 7A shows one variation of this embodiment, wherein the injector assembly includes spacer layer 701, which is conveniently a Kapton layer (hereinafter, "Kapton spacer layer 701"), between Pyrex plate 510 and the Kapton layer that forms flexible layer 508 of the injector assembly (hereinafter, "Kapton flexible layer 508").

Kapton spacer layer 701 has one hole 702 for each valve seat 703. The hole is typically about the same size and shape as valve seat 703. Each hole 702 is aligned with corresponding valve seat 703 so that Kapton flexible layer 701 is sufficiently spaced apart from Pyrex plate 510 in the area over valve seat 703 so that this area of Kapton flexible layer 701 does not stick to plate 510 upon heating.

Figure 7B:
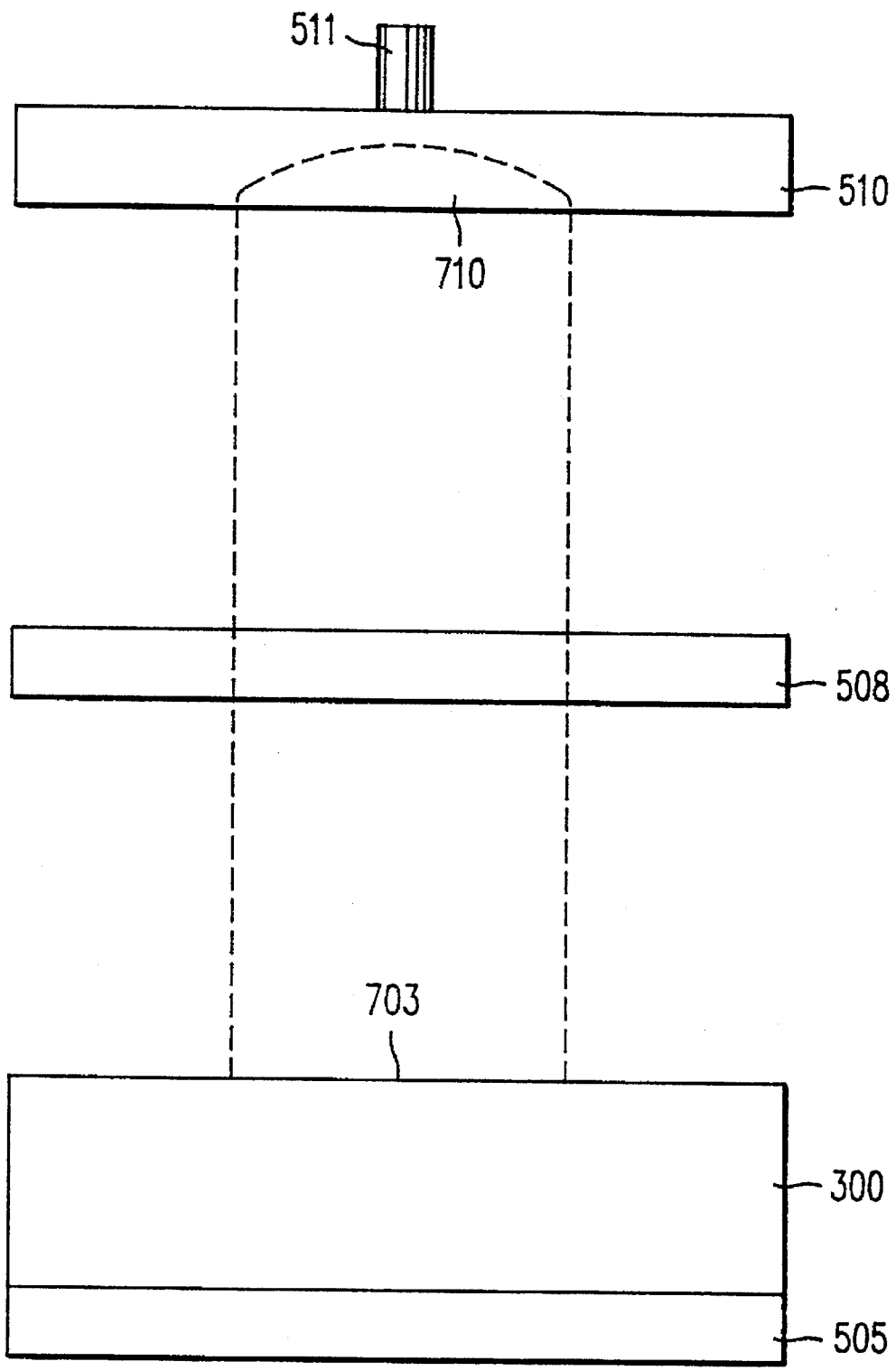

FIG. 7B shows a variation of the embodiment wherein the injector assembly produced by heating and pressing does not require a spacer layer. Rather, one well 710 for each valve seat 703 is etched in the surface of Pyrex plate 510 facing Kapton flexible layer 508. Each well 710 is approximately the same diameter as corresponding valve seat 703 and is aligned therewith. The well 710 should be deep enough to prevent the area of flexible Kapton layer 508 adjacent well 710 from sticking to Pyrex plate 510 upon heating. A depth of 0.003-inch (0.076-mm) generally provides satisfactory results. Any of several well-known methods for etching Pyrex can be used to form the wells.

Figure 7C:
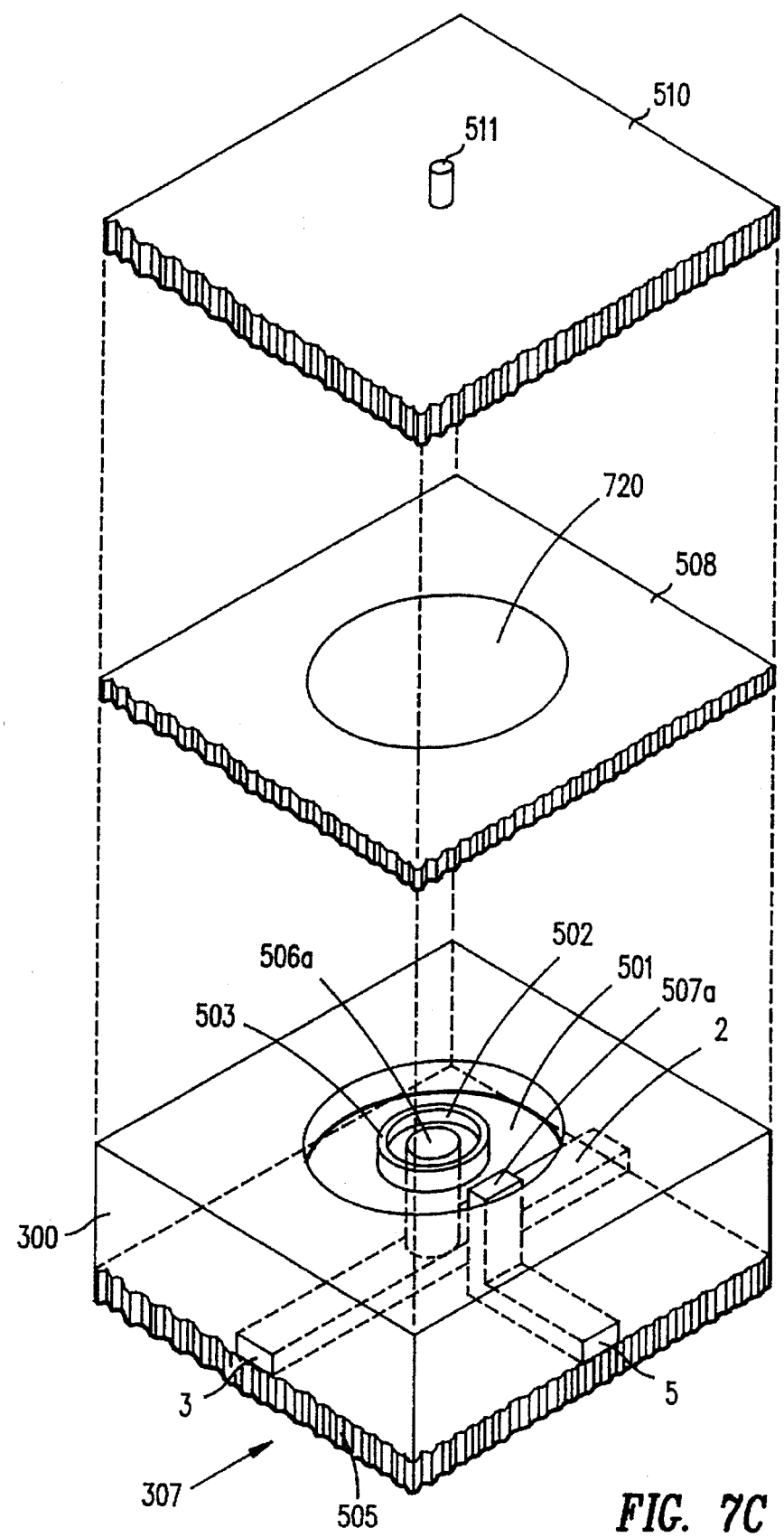

Referring to FIG. 7C, in another variation of this embodiment, an "anti-stick" substance is applied between Pyrex plate 510 and Kapton flexible layer 508 such that the areas of Kapton flexible layer 508 that form valve diaphragms, such as area 720, do not adhere to plate 510 upon heating. A substance to which Kapton flexible layer 508 does not stick can be applied to plate 510 and vice versa.

In another embodiment, the injector assembly can be produced using an adhesive to join inflexible layer 510 to flexible layer 508 and flexible layer 508 to wafer 300. In this production method, no adhesive is applied between inflexible layer 510 and flexible layer 508 in discrete areas, such as area 720 in FIG. 7C, so that the adjacent areas of flexible layer 508 form the valve diaphragms.

Conduction of gases into and out of the injector assembly is through holes in the inflexible layers and, in some instances, in the flexible layer. More specifically, inflexible layer 505 (FIG. 6A) contains holes to accommodate tubes connecting to ports 304, 309, 312, and 314 (FIG. 3). Inflexible layer 510 contains holes to accommodate tubes connecting to ports 301, 303, and 306. Holes in flexible layer 508 allow gases to pass between wafer 300 and the tubes in inflexible layer 510 that connect to ports 301, 303, and 306. Screens or filters can be placed in the holes in flexible layer 508 that connect to ports 301, 303, and 306 to prevent debris from entering the injector assembly. Inflexible layer 510 also contains ports, such as port 511 (FIG. 6A), for conducting a pressurized fluid to actuate the diaphragm valves.

Tubes for conducting the gases outside the injector assembly are typically bonded in the holes in the Pyrex plates. The tubes can be made of any suitable material, such as stainless steel. The tubes can be bonded to the Pyrex plate using any suitable adhesive. A UV-curing adhesive provides good results. Alternative bonding methods are possible, such as soldering, for example, when the inflexible layers are metal.

FIG. 3 is a micromachined microvalve injector assembly corresponding to the embodiment shown in FIG. 1. FIG. 3 shows the components of the injector assembly 10 in FIG. 1, with the addition of a reference gas outlet. In FIG. 3, four valve seats (purge/ foreflush valve 304, inject valve 307, sample valve 308, and backflush valve 310) and channels 1–8, 311, and 313 are formed on silicon wafer 300 by the conventional processes described above. Valves 304, 307, 308, and 310 correspond to valves 14, 17, 18, and 26 in FIG. 1, respectively.

FIGS. 6A and 6B are perspective views showing the structures of microvalves 307 and 308. In each microvalve, valve seats include annular recess 501, central recess 502, and annular ridge 503 between recesses 501 and 502. Flexible layer 508 is pressed against the valve seat side of wafer 300 to form the valve diaphragms. Inflexible layer 510 is pressed against flexible diaphragm 508, and inflexible layer 505 is bonded on the microchannel side of the wafer 300 to seal the micromachined grooves in wafer 300.

The control pressure that forces the flexible diaphragm to open and close each valve communicates with the flexible diaphragm through port 511 on plate 510. An orifice is formed in the center of central recess 502 communicating to a channel or channels formed on the microchannel side of the wafer 300. At least one through hole is formed in annular recess 501 communicating to a channel etched on the microchannel side. When pressure is applied through port 511, the diaphragm seats against the annular ridge 503 sealing the orifice. When the pressure is released, gas flows through the orifice between the channel connected to the orifice and the channel connected to the through hole in recess 501.

For inject valve 307, shown in FIG. 6A, channel 2 connects to channel 3 at valve orifice 506a on the microchannel side of wafer 300. Hole 507a couples inject valve 307 to channel 5. Thus, when inject valve 307 opens, channel 5 connects to channels 2 and 3. The structures of purge/foreflush valve 304 and backflush valve 310 are similar to inject valve 307, differing primarily in the shape and orientation of the channels that connect at each valve orifice on the microchannel side of wafer 300.

In sample valve 308, shown in FIG. 6B, valve orifice 506b communicates with channel 3 on the microchannel side of the wafer 300, and hole 507b communicates with channel 4. During sampling, when sample valve 308 opens, sample flows through hole 507b to valve orifice 506b, and then through channels 3, 2, and 1 to exit at port 301. Other microvalve structures are possible and can readily be devised by those skilled in the art.

In one embodiment of the present invention, the diaphragm of each microvalve is pressurized with helium gas to close the valves. When the helium pressure is released, the diaphragm relaxes to open the valves. The helium gas pressure applied to the diaphragm of each microvalve is controlled by associated conventional electrically-controlled solenoid valves (not shown). Generally, a helium pressure in the range of about 80 to about 100 psi is sufficient to control the diaphragm valves in this embodiment.

In FIG. 3, a sample source is connected to channel 4 at inlet port 303. Sample enters port 303 and is conducted to sample valve 308 via channel 4. Channels 1, 2, and 3, and the tubing and conduits (not shown) that connect port 301 to pressurization valve 53 (not shown) comprise the sample chamber. The volume of channel 2 from the orifice of purge/foreflush 304 to the orifice of the inject valve 307 corresponds to the fixed-volume of sample to be injected into the precolumn.

A tube conducts carrier fluid from the carrier fluid source (not shown) to port 306. The carrier fluid source provides a stable regulated head pressure of carrier fluid entering inlet port 306. In one embodiment, the carrier fluid pressure is about 20 psi at port 306. Channel 7 restricts the flow of carrier fluid between inlet port 306 and backflush valve 310. This flow restriction reduces the sensitivity of flow through channel 7 to pressure changes at the outlet to channel 7 as well as reducing the pressure of carrier fluid exiting channel 7.

Backflush valve 310 can be connected to a precolumn via channel 311 or 313. One end of the precolumn is connected to channel 313 at port 314 (or to channel 311 at port 312). The other end of the precolumn is connected at port 309 to channel 5, which connects to inject valve 307. An analytical column can be connected to channel 311 through port 312 (or to channel 313 at port 314).

The carrier fluid source also supplies pressurization and purge fluids. A tube (not shown) conducts pressurization/carrier fluid to a pressurization valve (not shown), and Channel 6 conducts purge/carrier fluid to purge/foreflush valve 304. In addition, an optional reference carrier fluid stream exits the injector assembly at port 305. Channel 8 restricts the flow of this stream from inlet port 306 to port 305, thereby reducing the sensitivity of flow through channel 8 to pressure changes at the outlet to channel 8. The reference carrier stream then passes through a thermal conductivity detector (shown schematically in FIGS. 1 and 2 as detector 21). If a reference carrier fluid stream is not required, port 305 and channel 8 are not required.

The sample can be pressurized, in which case it will flow into the sample chamber under its own pressure. Alternatively, the sample can be drawn in to the sample chamber using a vacuum pump connected to port 301. In this case, sample is drawn from port 303 to port 301 through channel 4, ample valve 308, and channels 3, 2, and 1. After sample fills the sample chamber, the sample is allowed to equilibrate for a selected dwell time. In one embodiment, the dwell time is about 140 milliseconds.

The sample in the sample chamber is then pressurized for a selected pressurization time by using the same carrier fluid source that supplies carrier fluid at port 306. In one embodiment, the pressurization time is about 340 milliseconds. After pressurization, purge/ foreflush valve 304 and inject valve 307 open and backflush valve 310 closes. Purge/carrier fluid passes through the orifice of purge/foreflush valve 304 and enters channel 2 as well as channel 1. The movement of carrier fluid into channel 1 forces the sample in channel 2 through open inject valve 307 and channel 5 and into a precolumn.

FIG. 4 is a micromachined microvalve injector assembly corresponding to the embodiment shown in FIG. 2. In this embodiment the elements for connection to a precolumn are replaced with channel 315 which directly connects inject valve 307 to backflush valve 310. FIG. 4 shows the components of the FIG. 2 injector assembly 10, with the addition of flow restrictions and a reference gas outlet.

The approximate dimensions of the important features in one micromachined-in-silicon embodiment shown in FIGS. 3 and 4 are as follows. Wafer 300 has a size 0.75 inches (19 mm) by 1.0 inches (25.4 mm), and a thickness of 0.012 inches (0.3 mm). Valve seats of diaphragm valves 304, 307, 308 and 310 have a 0.1 inch (2.5 mm) diameter.

The widths for channels 1–6 and 315 are 1 mm, 0.4 mm, 0.1 mm, 1 mm, 0.2 mm, 0.4 mm and 0.2 mm, respectively. The depth of each channel is 0.06 mm. The cross-sectional shape of the channels is rectangular. The volume of channel 2 is approximately 2 microliters. As the fixed-volume of sample injected is directly related to the volume of channel 2, the fixed-volume of sample injected can be varied by changing the length, width, or depth of channel 2. Channels 7 and 8 have a V-shape cross-section, with a depth of 0.04 mm and a top opening of 0.08 mm.

The distances between valves 307 and 308 and between valves 304 and 307 (designated in FIGS. 3 and 4 as "A" and "B", respectively) are 0.136 inch and 0.591 inch (3.45 mm and 15 mm), respectively. The diameters of the tubes for conducting gases into and out of the injector assembly are 0.020 to 0.028 inch (0.5 mm to 0.7 mm), with a 0.005-inch (0.13-mm) wall thickness. The flexible layer is a 0.003-inch (0.076-mm) thick layer of Dupont Kapton, which is 0.0005 inch (0.013 mm) Teflon, 0.002 inch (0.05 mm) polyimide, 0.0005 inch (0.013 mm) Teflon. The inflexible layers are 0.050-inch (1.3 mm) thick Pyrex plates.

As mentioned previously, reproducing the temperature of the sample in the chamber is desirable for high accuracy analyses, since the number of moles of gas in the sample chamber varies inversely with the temperature of the gas (absolute temperature). For example, in gas chromatography, a difference of 3° C. between the temperature of the calibration gas in the fixed-volume portion of the sample chamber during calibration and the temperature of the sample in the sample chamber during a subsequent analysis will result in a 1% error in the sample results (based on the ideal gas law PV=nRT).

To address this problem, one embodiment of the present invention includes heater 25, shown in FIGS. 1 and 2. Heater 25 heats the sample in sample chamber 11 to a predetermined temperature. Thus, sample in sample chamber 11 can be heated reproducibly to a desired temperature. In addition, the pressurization valve allows control of the sample pressure. The ability to precisely control sample temperature and pressure is particularly useful when the sample is a gas because such control ensures that the same number of moles of sample gas can be injected into the analytical column during repeated cycles of operation, providing high accuracy analyses.

In one embodiment, the heater is integrated into the injector assembly structure to heat and thermostatically control the injector assembly. In the micromachined embodiment shown in FIGS. 3 and 4, the heater comprises a resistive metal trace (the "heater trace") deposited on the surface of inflexible layer 510 (see FIGS. 6A and 6B) of the injector assembly near channel 2. A controlled electrical current is passed through the trace to heat the injector assembly. A nickel trace deposited on Pyrex glass provides good results. Another resistive metal trace (the "sensor trace") is deposited adjacent to the heater trace. The resistance of the sensor trace is detected and used to estimate the temperature of the injector assembly by well-known methods. The resistive metal heater trace is conventionally controlled to maintain a constant temperature.

In another embodiment, the heater comprises a layer containing a metal heater trace and a metal temperature sensing trace between two sheets of Kapton. A heater of this type can be purchased from Minco, Inc. This heater is attached with adhesive to inflexible layer 505 (see FIGS. 6A and 6B) on the side of inflexible layer 505 opposite the side next to wafer 300.

In one embodiment, the sample inlet tube and the port where the tube connects to the injector assembly are also heated to a controlled temperature by separately controlled resistive heating. For example, a thin-walled metal inlet tube can be heated resistively by direct application of electric current. The inlet port can be heated by a coil of resistive wire wrapped around it. Additional details of this type of heating are found in the copending and commonly owned application entitled "Heated-Zone Gas Chromatograph" (U.S. patent applicant Ser. No. 08/159,185 filed on Nov. 30, 1993), which is incorporated by reference herein.

To improve thermal control of the injector assembly, the injector assembly can be encased in thermally insulating potting material 316 (FIG. 3). A compound of silicone potting with glass microballoons provides excellent thermal insulation and adds mechanical strength to the assembly. The compound is prepared and used to encase the injector assembly by standard techniques. Briefly, glass microballoons (70 μm diameter, Fiber-Glast Developments, Inc.) are combined 1:1 (vol./vol.) with clear silicone potting resin (RTV 615, General Electric Company). The material is then cured according to the recommendations given for the silicone potting resin.

Although the present invention has been described and illustrated with particular embodiments, it is clearly understood that this is by way of illustration and example only and is not to be taken by way of limitation. Different modifications, variations and improvements can be made without departing from the spirit and scope of the invention. The spirit and scope of the present invention is limited only by the appended claims.

What is claimed is:

1. An injector assembly for injecting a fixed volume of a first fluid comprising:

a sample chamber for containing the first fluid and having a portion defining the fixed volume, said sample chamber having an open end adapted to connect to means for trapping the first fluid;

a first valve connected to said sample chamber at an end of the sample chamber opposite the open end, wherein said first valve is capable of conducting the first fluid from a first fluid source into said sample chamber;

a second valve connected to said sample chamber at one end of the fixed-volume portion, wherein said second valve is capable of conducting a second fluid from a second fluid source into said sample chamber;

a third valve connected to said sample chamber at an end of the fixed-volume portion opposite said second valve, wherein, in an injection mode of operation, said third valve is capable of conducting first fluid from the fixed-volume portion to an injection channel and, in a backflush mode of operation, said third valve is capable of conducting a third fluid from a third fluid source connected to said injection channel into said sample chamber; and a fourth valve between said injection channel and the third fluid source.

2. An injector assembly as in claim 1, wherein said means for trapping the first fluid comprises a fifth valve adapted to connect said sample chamber to a fourth fluid source so that fluid flow from the fourth fluid source is capable of pressurizing the first fluid to a predetermined pressure.

3. An injector assembly as in claim 2, wherein said fifth valve is additionally adapted to connect said sample chamber to a vacuum source for drawing the first fluid through said sample chamber.

4. An injector assembly as in claim 1, wherein said injection channel is adapted to connect to one end of a first column at a first connection point between said third valve and said fourth valve.

5. An injector assembly as in claim 4, wherein said injection channel is adapted to accommodate a detector between said first connection point and said third valve.

6. An injector assembly as in claim 4, wherein said injection channel comprises a first segment and a second segment, separated by a space, wherein the first segment is connected at one end to said third valve and unconnected at the other end, and the second segment is connected at one end to said connection point and unconnected at the other end, and each of the unconnected ends is adapted to be connected to one end of a second column.

7. An injector assembly as in claim 6, wherein said injection channel is adapted to accommodate a detector between said second column and said third valve.

8. An injector assembly as in claim 1, wherein a flow restriction is disposed between the third fluid source and said fourth valve.

9. An injector assembly as in claim 1, wherein said second, third, and fourth valves are T-valves.

10. An injector assembly as in claim 1, further comprising a heater in thermal contact with the fixed-volume portion of said sample chamber for heating any first fluid trapped therein to a predetermined temperature.

11. A micromachined, microvalve injector assembly for injecting a fixed volume of a first fluid comprising:
  a wafer-like substrate having two sides;
  a sample groove for containing the first fluid formed on one side of said substrate, a portion of said sample groove defining the fixed volume, said sample groove having an open end adapted to connect to means for trapping the first fluid;
  a first valve connected to said sample groove at an end of said sample groove opposite the open end, wherein said first valve is capable of conducting the first fluid from a first fluid source into said sample groove;
  a second valve connected to said sample groove at one end of the fixed-volume portion, wherein said second valve is capable of conducting a second fluid from a second fluid source into said sample groove;
  a third valve connected to said sample groove at an end of the fixed-volume portion opposite said second valve, wherein, in an injection mode of operation, said third valve is capable of conducting the first fluid from the fixed-volume portion to an injection groove and, in a backflush mode of operation, said third valve is capable of conducting a third fluid from a third fluid source connected to said injection groove into said sample groove;
  a fourth valve between said injection groove and the third fluid source, wherein said fourth valve is capable of conducting fluid from the third fluid source through said fourth valve, and wherein all of said valves have seats formed in said substrate;
  a first, inflexible layer overlying the portion of the substrate in which said sample and injection grooves are formed, thereby forming sample and injection channels, respectively; and
  a second, flexible layer overlying each of said valve seats, thereby serving as a diaphragm for each valve.

12. A micromachined, microvalve injector assembly as in claim 11, wherein all of said valves have seats formed in said substrate on a side opposite the sample and injection grooves.

13. A micromachined, microvalve injector assembly as in claim 11, wherein a third, inflexible layer overlies said second, flexible layer so that said second, flexible layer is disposed between the substrate and said third, inflexible layer.

14. A micromachined, microvalve injector assembly as in claim 11, wherein said means for trapping the first fluid comprises a fifth valve adapted to connect said sample channel to a fourth fluid source so that fluid flow from the fourth fluid source is capable of pressurizing the first fluid to a predetermined pressure.

15. A micromachined, microvalve injector assembly as in claim 14, wherein said fifth valve is additionally adapted to connect said sample channel to a vacuum source for drawing the first fluid through said sample channel.

16. A micromachined, microvalve injector assembly as in claim 11, wherein said injection channel is adapted to connect to one end of a first column at a first connection point between said third valve and said fourth valve.

17. A micromachined, microvalve injector assembly as in claim 16, wherein said injection channel is adapted to accommodate a detector between said first connection point and said third valve.

18. A micromachined, microvalve injector assembly as in claim 16, wherein said injection channel comprises a first segment and a second segment, separated by a space, wherein the first segment is connected on one end to said third valve and unconnected on the other end, and the second segment is connected on one end to said connection point and unconnected on the other end, and each of the unconnected ends is adapted to be connected to one end of a second column.

19. A micromachined, microvalve injector assembly as in claim 18, wherein said injection channel is adapted to accommodate a detector between said second column and said third valve.

20. A micromachined, microvalve injector assembly as in claim 11, wherein a flow restriction is disposed between the third fluid source and said fourth valve.

21. A micromachined, microvalve injector assembly as in claim 11, wherein said second, third, and fourth valves are T-valves.

22. A micromachined, microvalve injector assembly as in claim 11, further comprising a heater in thermal contact with the fixed-volume portion of said sample channel for heating any first fluid trapped therein to a predetermined temperature.

23. A micromachined, microvalve injector assembly as in claim 13 wherein a heater in thermal contact with the fixed-volume portion of said sample channel is incorporated into said third, inflexible layer.

24. A micromachined, microvalve injector assembly as in claim 22 wherein said heater comprises a first, resistive trace deposited on a surface of one of said layers.

25. A micromachined, microvalve injector assembly as in claim 24 wherein a second, resistive trace is deposited on a surface of one of said layers for sensing indirectly the temperature of the first fluid in the fixed-volume portion of said sample channel.

26. A micromachined, microvalve injector assembly as in claim 11 wherein a heater in thermal contact with the fixed-volume portion of said sample channel is attached to one of said layers, said heater comprising a heater trace and a temperature sensing trace disposed between two sheets of a flexible material.

27. A micromachined, microvalve injector assembly as in claim 11 wherein said micromachined, microvalve injector assembly is encased in a thermally insulating potting material.

28. A micromachined, microvalve injector assembly for injecting a fixed volume of a first fluid comprising:
  a wafer-like substrate having two sides;
  a sample groove for containing the first fluid formed on one side of said substrate, a portion of said sample groove defining the fixed volume, said sample groove having an open end adapted to connect to means for trapping the first fluid;
  a first valve connected to said sample groove at an end of said sample groove opposite the open end, wherein said first valve is capable of conducting the first fluid from a first fluid source into said sample groove;
  a second valve connected to said sample groove at one end of the fixed-volume portion, wherein said second valve is capable of conducting a second fluid from a second fluid source into said sample groove;

a third valve connected to said sample groove at an end of the fixed-volume portion opposite said second valve, wherein, in an injection mode of operation, said third valve is capable of conducting the first fluid from the fixed-volume portion to an injection groove formed on the same side of said substrate as said sample groove and, in a backflush mode of operation, said third valve is capable of conducting a third fluid from a third fluid source connected to said injection groove into said sample groove;

a fourth valve between said injection groove and the third fluid source, wherein said fourth valve is capable of conducting fluid from the third fluid source through said fourth valve, and wherein all of said valves have seats formed in said substrate on a side opposite the sample and injection grooves;

a first, inflexible layer overlying the portion of the substrate in which said sample and injection grooves are formed, thereby forming sample and injection channels, respectively, wherein said injection channel is adapted to connect to one end of a first column at a first connection point between said third valve and said fourth valve, and said injection channel comprises a first segment and a second segment, separated by a space, wherein the first segment is connected on one end to said third valve and unconnected on the other end, and the second segment is connected on one end to said first connection point and unconnected on the other end, and each of the unconnected ends is adapted to be connected to one end of a second column; and a second, flexible layer overlying the portion of the substrate in which the valve seats are formed, thereby serving as a diaphragm for each valve.

29. A micromachined, microvalve injector assembly as in claim 28, wherein a third, inflexible layer overlies said second, flexible layer so that said second, flexible layer is disposed between the substrate and said third, inflexible layer.

30. A micromachined, microvalve injector assembly as in claim 28, additionally comprising a heater in thermal contact with the fixed-volume portion of said sample channel for heating any first fluid trapped therein to a predetermined temperature.

31. A method for analyzing a first fluid by gas chromatography using backflushing comprising:

introducing the first fluid into a sample chamber of an injector assembly;

applying a second, pressurized fluid to the sample chamber to trap the first fluid in the sample chamber and to pressurize the first fluid to a predetermined pressure;

applying a third, pressurized fluid to the sample chamber to force a fixed volume of the first fluid out of the sample chamber and into a first column;

forcing the first fluid that exits the first column into a second column to separate components of the first fluid;

detecting the separated components of the first fluid; and after a selected time, applying a fourth, pressurized fluid to the first column, wherein the direction of flow through the first column is reversed and the direction of flow through the second column is the same as for the third, pressurized fluid.

32. A micromachined, microvalve injector assembly as in claim 22 wherein said heater in thermal contact with the fixed-volume portion of said sample channel is incorporated into one of said layers.

33. A gas chromatograph system for analyzing a fixed volume of a first fluid, comprising:

a sample chamber for containing the first fluid and having a portion defining the fixed volume, said sample chamber having an open end adapted to connect to means for trapping the first fluid;

a first valve connected to said sample chamber at an end of the sample chamber opposite the open end, wherein said first valve is capable of conducting the first fluid from a first fluid source into said sample chamber;

a second valve connected to said sample chamber at one end of the fixed-volume portion, wherein said second valve is capable of conducting a second fluid from a second fluid source into said sample chamber;

a third valve connected to said sample chamber at an end of the fixed-volume portion opposite said second valve;

an injection channel comprising first and second segments, each having first and second ends, wherein the first end of said first segment is connected to said third valve and the second end of said second segment defines a connection point, and wherein, in an injection mode of operation, said third valve is capable of conducting first fluid from the fixed-volume portion to said injection channel and, in a backflush mode of operation, said third valve is capable of conducting a third fluid into said sample chamber from a third fluid source connected to said injection channel at the connection point;

a fourth valve between the connection point and the third fluid source;

a precolumn connected at one end to the second end of said first injection channel segment and connected at an opposite end to the first end of said second injection channel segment, wherein said precolumn is back-flushed in the backflush mode of operation; and an analytical column connected at one end to said injection channel at the connection point.

34. A gas chromatograph system as in claim 33, comprising a single fluid source that serves as the second and third fluid sources.

35. A gas chromatograph system as in claim 34, wherein said means for trapping the first fluid comprises a fifth valve adapted to connect said sample chamber to a fourth fluid source so that fluid flow from the fourth fluid source is capable of pressurizing the first fluid to a predetermined pressure, said system further comprising a single fluid source that serves as the second, third, and fourth fluid sources.

36. A gas chromatograph system for analyzing a fixed volume of a first fluid comprising:

a wafer-like substrate having two sides;

a sample groove for containing the first fluid formed on one side of said substrate, a portion of said sample groove defining the fixed volume, said sample groove having an open end adapted to connect to means for trapping the first fluid;

a first valve connected to said sample groove at an end of the sample chamber opposite the open end, wherein said first valve is capable of conducting the first fluid from a first fluid source into said sample groove;

a second valve connected to said sample groove at one end of the fixed-volume portion, wherein said second valve is capable of conducting a second fluid from a second fluid source into said sample groove;

a third valve connected to said sample groove at an end of the fixed-volume portion opposite said second valve;

an injection groove comprising first and second segments, each having first and second ends, wherein the first end of said first segment is connected to said third valve and the second end of said second segment defines a connection point, and wherein, in an injection mode of operation, said third valve is capable of conducting first fluid from the fixed-volume portion to said injection groove and, in a backflush mode of operation, said third valve is capable of conducting a third fluid into said sample groove from a third fluid source connected to said injection groove at the connection point; and a fourth valve between the connection point and the third fluid source, wherein said fourth valve is capable of conducting fluid from the third fluid source through said fourth valve, and wherein all of said valves have seats formed in said substrate;

a first, inflexible layer overlying the portion of the substrate in which said sample and injection grooves are formed, thereby forming sample and injection channels, respectively;

a second, flexible layer overlying each of said valve seats, thereby serving as a diaphragm for each valve;

a precolumn connected at one end to the second end of said first injection channel segment and connected at an opposite end to the first end of said second injection channel segment, wherein said precolumn is backflushed in the backflush mode of operation;

an analytical column connected at one end to said injection channel at the connection point.

37. A gas chromatograph system as in claim 36, comprising a single fluid source that serves as the second and third fluid sources.

38. A gas chromatograph system as in claim 37, wherein said means for trapping the first fluid comprises a fifth valve adapted to connect said sample channel to a fourth fluid source so that fluid flow from the fourth fluid source is capable of pressurizing the first fluid to a predetermined pressure, said system further comprising a single fluid source that serves as the second, third, and fourth fluid sources.

39. An injector assembly as in claim 1, wherein said second valve is connected to said sample chamber at an end of the fixed-volume portion proximal to the open end of said sample chamber and distal to said first valve.

40. An injector assembly as in claim 11, wherein said second valve is connected to said sample chamber at an end of the fixed-volume portion proximal to the open end of said sample chamber and distal to said first valve.

* * * * *